United States Patent
Boal

(10) Patent No.: US 10,172,360 B2
(45) Date of Patent: Jan. 8, 2019

(54) METHODS FOR THE DIRECT ELECTROLYTIC PRODUCTION OF STABLE, HIGH CONCENTRATION AQUEOUS HALOSULFAMATE OR HALOSULFONAMIDE SOLUTIONS

(71) Applicant: Johnson Matthey Public Limited Company, London (GB)

(72) Inventor: Andrew K. Boal, Albuquerque, NM (US)

(73) Assignee: Johnson Matthey Public Limited Company, London (GB)

(*) Notice: Subject to any disclaimer, the term of this patent is extended or adjusted under 35 U.S.C. 154(b) by 110 days.

(21) Appl. No.: 14/964,504

(22) Filed: Dec. 9, 2015

(65) Prior Publication Data

US 2016/0157494 A1 Jun. 9, 2016

Related U.S. Application Data

(60) Provisional application No. 62/089,770, filed on Dec. 9, 2014.

(51) Int. Cl.
*A01N 59/02* (2006.01)
*C25B 1/00* (2006.01)
*A01N 59/00* (2006.01)

(52) U.S. Cl.
CPC .............. *A01N 59/02* (2013.01); *A01N 59/00* (2013.01)

(58) Field of Classification Search
CPC ........ A01N 59/02; A01N 59/00; A01N 25/22; A01N 59/08; C25B 1/24; C25B 11/02; C25B 1/26; C25B 1/30; C25B 3/06; C25B 9/00; C25B 15/02
See application file for complete search history.

(56) References Cited

U.S. PATENT DOCUMENTS

| | | |
|---|---|---|
| 1,029,580 A | 6/1912 | Bane |
| 1,200,165 A | 10/1916 | Burgess |
| 1,806,801 A | 5/1931 | Higgins |
| 2,256,958 A | 9/1941 | Muskat |
| 2,256,959 A | 9/1941 | Muskat |
| 2,438,781 A | 3/1948 | Kamlet |
| 2,473,986 A | 6/1949 | Booth |
| 2,666,010 A | 1/1954 | Stayner |
| 2,679,533 A | 5/1954 | Darragh et al. |
| 2,987,435 A | 6/1961 | Davies et al. |
| 3,222,269 A | 12/1965 | Stanton |
| 3,234,110 A | 2/1966 | Beer |
| 3,254,952 A | 6/1966 | Raleigh et al. |
| 3,329,609 A | 4/1967 | Blomfield |
| 3,328,298 A | 6/1967 | Asseff |
| 3,365,061 A | 1/1968 | Bray |
| 3,505,215 A | 4/1970 | Bray |
| 3,558,503 A | 1/1971 | Goodenough et al. |
| 3,616,355 A | 10/1971 | Themy et al. |
| 3,622,479 A | 11/1971 | Schneider |
| 3,654,148 A | 4/1972 | Bradley |
| 3,749,524 A | 7/1973 | Jordan |
| 3,776,825 A | 12/1973 | Vit |
| 3,791,768 A | 2/1974 | Wanner |
| 3,825,122 A | 7/1974 | Taylor |
| 3,904,496 A | 9/1975 | Harke et al. |
| 3,932,296 A | 1/1976 | Byth |
| 4,000,065 A | 12/1976 | Ladha et al. |
| 4,070,280 A | 1/1978 | Bray |
| 4,077,883 A | 3/1978 | Bray |
| 4,110,180 A | 8/1978 | Nidola et al. |
| 4,124,488 A | 11/1978 | Wilson |
| 4,138,210 A | 2/1979 | Avedissian |
| 4,151,092 A | 4/1979 | Grimm et al. |
| 4,167,561 A | 9/1979 | Lamberti et al. |
| 4,187,173 A | 2/1980 | Keefer |
| 4,212,714 A | 7/1980 | Coker et al. |
| 4,240,884 A | 12/1980 | Pellegri |
| 4,288,326 A | 9/1981 | Keefer |
| 4,290,873 A | 9/1981 | Weaver |

(Continued)

FOREIGN PATENT DOCUMENTS

| | | |
|---|---|---|
| GB | 2409684 | 6/2005 |
| JP | 02111708 | 4/1990 |
| JP | 06246273 | 9/1994 |
| JP | 2000005757 | 1/2000 |
| JP | 2000093961 | 4/2000 |
| JP | 2001198573 | 7/2001 |
| JP | 200252074 | 2/2002 |
| JP | 2004130264 | 4/2004 |
| WO | 9114647 | 10/1991 |
| WO | 2004084698 A2 | 10/2004 |
| WO | 2006103314 A1 | 10/2006 |
| WO | 2008091678 | 7/2008 |
| WO | 2013093915 | 6/2013 |

OTHER PUBLICATIONS

Audrieth, et al., "The Stability of Aqueous Chloramine Solutions", J. Am. Chem. Soc., 1955, 4726-4728.
Benson, et al., "Sulfamic Acid and Its N-Substituted Derivatives", Chem. Rev., 1980, 151-186.
El Maghraby, et al., "Quaternary ammonium salt as effective corrosion inhibitor for carbon steel dissolution in sulphuric acid media", Advances in Applied Science Research, 2010, 1 (2), Pelagia Research Library, 2010, 143-155.

(Continued)

*Primary Examiner* — Robert A Wax
*Assistant Examiner* — Olga V Tcherkasskaya
(74) *Attorney, Agent, or Firm* — Baker & Hostetler LLP

(57) ABSTRACT

Methods and apparatuses for the direct electrochemical generation of high concentration, stable aqueous solutions comprised of mixtures of free halogen species, N-halosulfamate compounds, N-halosulfonamide, and other compounds for biocidal applications is disclosed. Solutions containing the desired content of these species, with the desired concentration and pH value, is achieved through the electrolysis of aqueous brines containing mixtures of metal halide compounds, sulfamic acid, and other additives as desired. Controlling the relative compositions of the brines used to prepare the desired biocidal solutions, as well as the electrolysis conditions, can produce the biocidal solution with the desired composition and properties.

20 Claims, 3 Drawing Sheets

(56) References Cited

U.S. PATENT DOCUMENTS

| | | |
|---|---|---|
| 4,306,952 A | 12/1981 | Jansen |
| 4,321,137 A | 3/1982 | Kohler |
| 4,333,805 A | 6/1982 | Davidson et al. |
| 4,367,140 A | 1/1983 | Wilson |
| 4,389,311 A | 6/1983 | La Freniere |
| 4,432,876 A | 2/1984 | Keefer |
| 4,434,056 A | 2/1984 | Keefer |
| 4,496,443 A | 1/1985 | Mack et al. |
| 4,534,713 A | 8/1985 | Wanner |
| 4,536,292 A | 8/1985 | Matz |
| 4,560,455 A | 12/1985 | Porta et al. |
| RE32,077 E | 2/1986 | Denora et al. |
| RE32,144 E | 5/1986 | Keefer |
| 4,632,754 A | 12/1986 | Wood |
| 4,722,263 A | 2/1988 | Valentin |
| 4,724,079 A | 2/1988 | Sale et al. |
| 4,744,877 A | 5/1988 | Maddock |
| 4,756,830 A | 7/1988 | Fredkin |
| 4,759,844 A | 7/1988 | Lipschultz et al. |
| 4,759,852 A | 7/1988 | Trulear |
| 4,761,208 A | 8/1988 | Gram |
| 4,786,380 A | 11/1988 | Van Duin et al. |
| 4,790,923 A | 12/1988 | Stillman |
| 4,790,946 A | 12/1988 | Jansen |
| 4,836,924 A | 6/1989 | Solomon |
| RE33,135 E | 12/1989 | Wanner, Sr. et al. |
| 4,973,408 A | 11/1990 | Keefer |
| 4,976,842 A | 12/1990 | Fowler |
| 5,085,753 A | 2/1992 | Sherman |
| 5,089,096 A | 2/1992 | Rijkhof et al. |
| 5,112,487 A | 5/1992 | Himeshima et al. |
| 5,207,916 A | 5/1993 | Goheen et al. |
| 5,221,451 A | 6/1993 | Seneff et al. |
| 5,244,579 A | 9/1993 | Horner et al. |
| 5,254,226 A | 10/1993 | Williams et al. |
| 5,259,950 A | 11/1993 | Shiro et al. |
| 5,306,428 A | 4/1994 | Tonner |
| 5,320,718 A | 6/1994 | Molter et al. |
| 5,354,264 A | 10/1994 | Bae et al. |
| 5,358,635 A | 10/1994 | Frank et al. |
| 5,385,711 A | 1/1995 | Baker et al. |
| 5,429,723 A | 7/1995 | Atkinson |
| 5,462,644 A | 10/1995 | Woodson |
| 5,480,386 A | 1/1996 | Brohy |
| 5,492,534 A | 2/1996 | Athayde et al. |
| 5,496,466 A | 3/1996 | Gray |
| 5,503,736 A | 4/1996 | Schoenmeyr |
| 5,531,887 A | 7/1996 | Miers |
| 5,534,145 A | 7/1996 | Platter et al. |
| 5,540,848 A | 7/1996 | Engelhard |
| 5,558,762 A | 9/1996 | Fife et al. |
| 5,581,189 A | 12/1996 | Brenn |
| 5,597,482 A | 1/1997 | Melyon |
| 5,611,938 A | 3/1997 | Smolik et al. |
| 5,679,239 A | 10/1997 | Blum et al. |
| 5,685,980 A | 11/1997 | Patapoff et al. |
| 5,725,758 A | 3/1998 | Chace et al. |
| 5,795,459 A | 8/1998 | Sweeney |
| 5,858,201 A | 1/1999 | Otsuka et al. |
| 5,868,911 A | 2/1999 | Blum et al. |
| 5,900,212 A | 5/1999 | Maiden et al. |
| 5,911,870 A | 6/1999 | Hough |
| 5,928,490 A | 7/1999 | Sweeney |
| 5,958,229 A | 9/1999 | Filiopoulos et al. |
| 5,976,386 A | 11/1999 | Barak |
| 5,989,396 A | 11/1999 | Prasnikar et al. |
| 6,007,686 A | 12/1999 | Welch et al. |
| 6,110,424 A | 8/2000 | Maiden et al. |
| 6,132,628 A | 10/2000 | Barak |
| 6,149,835 A | 11/2000 | Brown |
| 6,162,371 A | 12/2000 | Rees et al. |
| 6,180,014 B1 | 1/2001 | Salama |
| 6,309,523 B1 | 10/2001 | Prasnikar et al. |
| 6,313,049 B1 | 11/2001 | Heady et al. |
| 6,471,974 B1 | 10/2002 | Rees et al. |
| 6,524,475 B1 | 2/2003 | Herrington et al. |
| 6,632,336 B2 | 10/2003 | Kasuya |
| 6,632,347 B1 | 10/2003 | Buckley et al. |
| 6,660,307 B2 | 12/2003 | Zolotarsky et al. |
| 6,669,904 B1 | 12/2003 | Yang |
| 6,716,805 B1 | 4/2004 | Sherry et al. |
| 6,736,966 B2 | 5/2004 | Herrington et al. |
| 6,773,575 B2 | 8/2004 | Nakajima et al. |
| 7,008,523 B2 | 3/2006 | Herrington |
| 7,045,153 B2 | 5/2006 | Howarth et al. |
| 7,048,842 B2 | 5/2006 | Tremblay et al. |
| 7,067,063 B2 | 6/2006 | Barak |
| 7,195,782 B2 | 3/2007 | Moore et al. |
| 7,204,931 B2 | 4/2007 | Martin et al. |
| 7,285,224 B2 | 10/2007 | Barak |
| 7,309,503 B2 | 12/2007 | Howarth et al. |
| 7,311,878 B2 | 12/2007 | Singleton et al. |
| 7,387,736 B2 | 6/2008 | Phillips et al. |
| 7,455,859 B2 | 11/2008 | Howarth et al. |
| 7,767,095 B2 | 8/2010 | Phillips et al. |
| 7,922,890 B2 | 4/2011 | Sanchez et al. |
| 8,574,605 B2 | 11/2013 | Howarth et al. |
| 8,741,157 B2 | 6/2014 | Wetegrove et al. |
| 8,747,740 B2 | 6/2014 | Sharoyan et al. |
| 2002/0172725 A1* | 11/2002 | Zolotarsky ............. A01N 59/00 424/688 |
| 2004/0060815 A1 | 4/2004 | Buckley et al. |
| 2006/0029680 A1* | 2/2006 | Harvey .................. A61K 33/00 424/600 |
| 2006/0051284 A1 | 3/2006 | Fishler et al. |
| 2006/0157343 A1 | 7/2006 | Herrington |
| 2007/0125714 A1 | 6/2007 | Reddy |
| 2008/0017519 A1 | 1/2008 | Siemer et al. |
| 2008/0108537 A1 | 5/2008 | Rees |
| 2008/0160604 A1 | 7/2008 | Gupta et al. |
| 2008/0181815 A1* | 7/2008 | Cheng ....................... C02F 1/50 422/37 |
| 2008/0190763 A1 | 8/2008 | Del Signore |
| 2009/0062156 A1 | 3/2009 | Wilson et al. |
| 2009/0110749 A1 | 4/2009 | Norton et al. |
| 2009/0214674 A1 | 8/2009 | Barraud et al. |
| 2009/0311164 A1 | 12/2009 | Gupta et al. |
| 2010/0240535 A1* | 9/2010 | Yoneda .................. A01N 59/00 504/151 |
| 2011/0272304 A1 | 11/2011 | Wahal et al. |
| 2012/0021062 A1 | 1/2012 | Gupta et al. |
| 2012/0228149 A1 | 9/2012 | Boal et al. |
| 2012/0328504 A1 | 12/2012 | Debiemme-Chouvy |
| 2013/0189379 A1* | 7/2013 | Nalepa .................. A01N 59/00 424/723 |
| 2014/0018432 A1 | 1/2014 | Sharoyan |
| 2014/0322362 A1 | 10/2014 | Frim |

OTHER PUBLICATIONS

Lyalin, et al., "Developing Principles for an Electrochemical Low-Waste Production of Chloramines T, B, and KhB", Russian Journal of Electrochemistry, 2000, 1246-1256.

Meakins, "Alkyl Quaternary Ammonium Compounds as Inhibitors of the Acid Corrosion of Stell", Journal of Applied Chemistry, vol. 13, Issue 8, Aug. 1963, 339-345.

Niu, et al., "Corrosion inhibition of iron in acidic solutions by alkyl quaternary ammonium halides: Correlation between inhibition effciency and molecular structure", Applied Surface Science, vol. 252, Issue 5, Dec. 15, 2005, 1634-1642.

Rimassa, et al., "Are You Buying Too Much Friction Reducer Because of Your Biocide?", SPE Hydraulic Fracturing Technology Conference, 2009, 2009, 1-9.

Venczel, "Inactivation of Cryptosporidium parvum Oocysts and Clostridium perfringens Spores by a Mixed-Oxidant Disinfectant and by Free Chlorine", Applied and Environmental Microbiology, Apr. 1997, 1598-1601.

Vert, et al., "Terminology for biorelated polymers and applications (IUPAC Recommendations 2012)", Pure Appl. Chem., 2012, 377-410.

Sobsey et al., "Inactivation of Cryptosporidium parvum Oocysts and other Waterborne Microbes by Oxidants Generated Electro-

(56) References Cited

OTHER PUBLICATIONS chemically from Sodium Chloride from Portable Pen and Bench Scale Systems", American Water Works Association, Water Quality Technology Conference Proceedings, Nov. 5-9, 2000, Salt Lake City, UT, 9 Pages.

* cited by examiner

METHODS FOR THE DIRECT ELECTROLYTIC PRODUCTION OF STABLE, HIGH CONCENTRATION AQUEOUS HALOSULFAMATE OR HALOSULFONAMIDE SOLUTIONS

CROSS-REFERENCE TO RELATED APPLICATIONS

This application claims priority to and the benefit of filing of U.S. Provisional Patent Application Ser. No. 62/089,770, entitled "Methods for the Direct Electrolytic Production of Stable, High Concentration Aqueous Halosulfamate or Halosulfonamide Solutions", filed on Dec. 9, 2014, the specification and claims of which are incorporated herein by reference.

BACKGROUND OF THE INVENTION

Field of the Invention (Technical Field)

The present invention is related to the in situ production of high concentration stable aqueous biocidal solutions comprised of mixtures of free halogens, N-halosulfamic acid compounds, N-halosulfamate compounds, N,N-dihalosulfamic acid compounds and N,N-dihalosulfamate compounds, with or without additional biocidally active components, in any desired compositional mixture and at a desired pH through an electrolysis process, where the nature of the biocidal solution is determined by the nature of the brine used in the electrolysis process as well as the operational parameters of the electrolytic process.

Background Art

Note that the following discussion may refer to a number of publications and references. Discussion of such publications herein is given for more complete background of the scientific principles and is not to be construed as an admission that such publications are prior art for patentability determination purposes.

Aqueous free halogen species such as chlorine, bromine, iodine, hypochlorous acid, hypobromous acid, hypoiodous acid, hypochlorite, hypobromite, and hypoiodite are known to be very powerful anti-microbial agents and are often used in water disinfection applications. Along with a high level of biocidal activity, aqueous free halogens are also highly chemically reactive to other species often present in waters undergoing treatment. These species include natural organic matter, synthetic and natural organic chemicals, iron, manganese, hydrogen sulfide, ammonia, arsenic, and other chemicals. The presence of these free halogen demanding substances consume free halogens added to the water that would otherwise be useful in inactivating microorganisms, thus, this process could be considered detrimental to the overall treatment process if the free halogen consuming chemical reaction is not desirable. Reactions between aqueous free halogens and organic material present in the water being treated can also, in some cases, lead to the undesirable products such as the formation of halogenated organic chemicals such as trihalomethanes and haloacetic acids. Therefore, the treatment of waters containing high amounts of these halogen-reactive compounds is often advantageously accomplished through the use of biocides that are less chemically reactive than aqueous free halogen species.

Haloamines, which can broadly be considered as chemical species which contain at least one nitrogen-halogen bond, are often used in place of oxidizing free halogens to provide a disinfectant for water treatment. While haloamines are effective biocidal compounds, they are also much less chemically reactive as compared to free halogens. Thus, in waters containing substantial amounts of free halogen demanding substances, haloamines have the potential to provide a substantial benefit to the overall water disinfection process. Aqueous solutions of haloamines are typically produced through a chemical reaction between an aqueous free halogen species and a compound containing at least one nitrogen-hydrogen bond whereby the chemical reaction produces a compound containing at least one nitrogen-halogen bond. Ammonia or ammonium ions are the most common source of the nitrogen containing compound used in this process, although other nitrogen containing compounds are often utilized as well.

One major deterrent to the use of haloamines, and especially haloamines produced through the reaction of ammonia or ammonium ions with an aqueous free halogen species, is that they are highly unstable, especially at higher concentrations (i.e. greater than 10 mg/L); see for example Audrieth, L. F.; Rowe, R. A. "The Stability of Aqueous Chloramine Solutions" J. Am. Chem. Soc. 1955, 77, 4726-4728. Due to the instability of haloamines, it is typically not possible to produce concentrated haloamine solutions and ship them to a point of application. As a result, haloamines derived from ammonia or ammonium ions are often produced in situ during treatment by the action of aqueous free halogens on ammonia or organic amines naturally present or added to water being treated. Alternatively, it is sometimes desirable to prepare concentrated aqueous haloamine solutions derived from the reaction between ammonia or ammonium ions at the point of application and then use these formed haloamine solutions as a primary disinfectant. Situations where this could be advantageous include the treatment of waters which have a known or highly variable free halogen demand which would consume free halogens without the benefit of microbial inactivation but which can be effectively treated with a haloamine disinfectant.

Sulfamic acid and its organic compound derivatives, known as sulfonamides (for example, toluenesulfonamide), are chemically distinct from ammonia or other organic amine-containing compounds used to produce haloamines but, like ammonia or many amines, typically contain a nitrogen-hydrogend bond which can react with aqueous halogen species. Products of the reaction between sulfamic acid, having the chemical formula $H_3NSO_3$, and an aqueous halogen species are N-halosulfamate compounds (either N-halosulfamate, having the chemical formula $HNSO_3X^-$, or N-halosulfamic acid, having the chemical formula $H_2NSO_3X$), N,N-dihalosulfamate compounds (N,N-dihalosulfamic acid, having the chemical formula $HNSO_3X_2$, or N,N-dihalosulfamate, having the chemical formula $NSO_3X_2^-$), or combinations thereof, where, in all cases, the letter X represents a halogen (i.e. Cl, Br, I). Products of the reaction between and organic sulfonamide compounds, having the chemical formula of $RSO_2NH_2$, and an aqueous halogen species are N-halosulfanomide compounds, having the chemical formula of $RSO_2NHX$, N,N-dihalosulfonamide compounds, having the chemical formula of $RSO_2NX_2$, or combinations thereof, where, in all cases, the letter R represents and organic functional group comprising at least carbon and hydrogen and the letter X represents a halogen (i.e. Cl, Br, I). These compounds can stabilize the electrolyzed halogen species.

U.S. Pat. No. 3,776,825 to Vit entitled "Electrolytic Treatment" discloses that a brine comprising a halide ion source and an amine compound both dissolved in water is first pH adjusted through the addition of a base such as sodium hydroxide, and then electrolyzed, thereby producing a solution containing one or more haloamine compound, including N-chlorosulfamates or N-chlorosulfonamides produced from sulfamic acid or organic sulfonamides, respectively. Vit further teaches that when electrolysis is used to make these haloamine solutions they are unstable, and therefore the invention descried by Vit is focused entirely on the instantaneous production and immediate subsequent use of the produced haloamines as opposed to the production of stable haloamine solutions. Because Vit discloses the addition of NaOH to the brine prior to electrolysis, and discloses that the pH of the solution is thus greater than 12, the solution prior to electrolysis no longer comprises sulfamic acid, but instead comprises sulfamate ions.

SUMMARY OF THE INVENTION
(DISCLOSURE OF THE INVENTION)

The present invention is a method for producing a stable disinfecting solution comprising a plurality of halosulfamate and/or halosulfamic acid species and one or more halogen species, the method comprising preparing an acidic solution comprising desired concentrations of halide ions and sulfamic acid and electrolyzing the solution, wherein the concentrations of the halide ions and the sulfamic acid in the acidic solution and the pH of the acidic solution are chosen to produce the desired concentrations of the halosulfamate species and/or halosulfamic acid species in the stable disinfecting solution. The acidic solution optionally further comprises one or more additional halogen stabilizing compounds. The one or more additional halogen stabilizing compounds are preferably selected from the group consisting of lithium sulfamate, sodium sulfamate, potassium sulfamate, organic sulfonamide, methylsulfonamide, o-toluenesulfonamide, m-toluenesulfonamide, p-toluenesulfonamide, cyanuric acid, a derivative of cyanuric acid, succinimide, a derivative of succinimide, hydantoin, a derivative of hydantoin, and combinations thereof. The stable disinfecting solution can then optionally comprise N-halosulfonamide compounds and/or N,N-dihalosulfonamide compounds. The halosulfamate species preferably comprise N-halosulfamate compounds and/or N,N-dihalosulfamate compounds, and the halosulfamic acid species preferably comprise N-halosulfamic acid compounds and/or N,N-dihalosulfamic acid compounds. The stable disinfecting solution is preferably a high concentration solution. The acidic solution preferably does not comprise a non-amine base.

The preparing step optionally comprises providing a salt blend comprising sulfamic acid and one or more salts comprising the halide ions and diluting the salt blend with water. The salt blend preferably comprises a pellet, briquette, or compacted form, preferably comprises a solid solution, and optionally comprises an anti-caking agent. The method preferably further comprises flowing the acidic solution through an electrolytic cell at a flow rate selected to produce the desired pH of the stable disinfecting solution. The flow rate can optionally be increased, thereby maintaining the acidity of electrolyte in the vicinity of cathodes in the electrolytic cell during the electrolyzing step, which then preferably results in removing scale from surfaces of the cathodes or preventing the formation of scale on the surfaces of the cathodes. The pH of the acidic solution is preferably less than 4, and more preferably less than 1. The pH of the stable disinfecting solution is optionally greater than 9, or optionally greater than 11, or optionally less than 3.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating certain embodiments of the invention and are not to be construed as limiting the invention. In the drawings.

DETAILED DESCRIPTION OF EMBODIMENTS OF THE INVENTION

Figure 1:
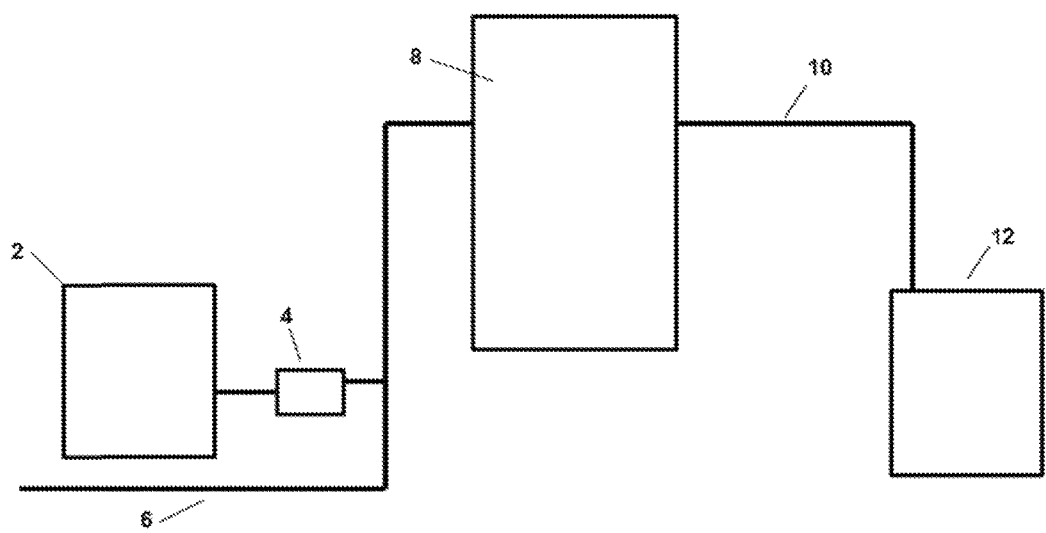
FIG. 1 is a schematic drawing of a system for the production of stable, concentrated aqueous solutions comprised of free halogen species, N-halosulfamate compounds, N,N-dihalosulfamate compounds, N-halosulfonamide compounds, N,N-dihalosulfonamide compounds from a single, highly concentrated brine source that is diluted into a process water.

Embodiments of the present invention are simplified electrochemically-driven processes whereby controlled formation and electrolysis of specifically designed aqueous brine blends comprising metal halide salts combined with at least sulfamic acid either alone or in combination with other halogen stabilizing compounds in a single electrolysis step are used to produce stable, high concentration aqueous solutions comprised of at least halogens, N-halosulfamate compounds, N,N-dihalosulfamate compounds, or other stabilized compounds, in any desired compositional blend. Production of these solutions is preferably achieved through precise control of the composition of the brines, used in the electrolysis process as well as electrolytic conditions used to electrolyze the brines.

As used throughout the specification and claims, the term "high concentration" means a solution with a total halogen content of at least 2100 mg/L. Total halogen content includes free halogen species, N-halosulfamate compounds, and N,N-dihalosulfamate compounds. As used throughout the specification and claims, the term "stable" means a solution with less than a 5% loss in total halogen content over a 24 hour time period. As used throughout the specification and claims, the term "non-amine base" means any basic compound that does not comprise an amine, such as sodium hydroxide, potassium hydroxide, sodium bicarbonate, or calcium carbonate. The present invention can be used to provide halogen-based disinfectant solutions wherever such solutions can be useful for microbiological control, and will be especially useful in the disinfection of highly challenging waters such as those found in oil and gas production processes, industrial cooling systems, pulp and paper production facilities, and food and beverage production processes. Embodiments of the present invention are directed to electrolysis processes of brines comprising mixtures of sodium chloride, sodium bromide, and sulfamic acid, although other metal halide sources can be used in place of sodium chloride or sodium bromide, and other halogen stabilizing compounds can be used instead of or in addition to sulfamic acid.

Metal halide brines subjected to electrolysis undergo several electrolytic and chemical transformations, starting with the electrolytic oxidation of halide ions to produce halogens:

$$2X^- - 2e^- \rightarrow X_2$$

where $X^-$ is the halide ion and $X_2$ is the diatomic, molecular halogen. Here, $X^-$ can be $Cl^-$, $Br^-$, $I^-$, or any combination thereof while $X_2$ can be $Cl_2$, $Br_2$, $I_2$, $BrCl$, $BrI$, $ICl$, or any combination thereof. Once the $X_2$ halogen species is formed by the electrolysis process, it will react with water also present in the brine to produce a combination of acids:

$$X_2 + H_2O \rightarrow HX + HOX$$

where $H_2O$ is water, HX is a hydrohalic acid, and HOX is a hypohalous acid. Here, HX can be HCl, HBr, HI, or any combination thereof while HOX can be HOCl, HOBr, HOI, or any combination thereof. Depending on the pH of the brine during electrolysis and/or the pH of the electrolyzed solution, the hypohalous acid component of the electrolyzed solution can disassociate to yield hypohalite ions according to:

$$HOX \leftrightarrow H^+ + XO^-$$

where $XO^-$ is the hypohalite ion, such as $ClO^-$, $BrO^-$, $IO^-$, or any combination thereof, depending on the halide ion content of the brine. The relative amount of HOX and $XO^-$ present in the brine during electrolysis and the electrolyzed solution varies according to the acid disassociation constants of the various hypohalous acids. In this process, $X_2$, HOX, and $XO^-$ are all considered to be free halogen species.

In the presence of sulfamic acid, these chlorine species will participate in a sequence of chemical reactions that will yield N-chlorosulfamic acid, N-chlorosulfamate, N,N-dichlorosulfamic acid, and N,N-dichlorosulfamate. An example of this is the reaction between hypochlorous acid and sulfamic acid:

$$HOCl + H_2NSO_3H \rightarrow ClHNSO_3H + H_2O$$

$$HOCl + ClHNSO_3H \rightarrow Cl_2NSO_3H + H_2O.$$

In other words, when sulfamic acid, having a chemical formula of $H_3NSO_3$, is present in the brine during electrolysis, it will react with the free halogen species present in the electrolyzed brine to produce N-halosulfamic acids, having chemical formulas of $H_2NSO_3X$, N-halosulfamates, having chemical formulas of $HNSO_3X^-$, N,N-dihalosulfamic acids, having chemical formulas of $HNSO_3X_2$, and N,N-dihalosulfamates, having chemical formulas of $NSO_3X_2^-$ where, in all cases, X represents halogens such as chlorine (Cl), bromine (Br), and/or iodine (I). Depending on the composition of the brine used in the present invention, the biocidal composition of the electrolyzed solutions can contain chlorine ($Cl_2$), bromine ($Br_2$), iodine ($I_2$), bromine monochloride (BrCl), bromine monoiodide (BrI), iodine monochloride (ICl) hypochlorous acid (HOCl), hypobromous acid (HOBr), hypoiodous acid (HOI), hypochlorite ($ClO^-$), hypobromite ($BrO^-$), hypoiodite ($IO^-$), N-chlorosulfamic acid ($H_2NSO_3Cl$), N-bromosulfamic acid ($H_2NSO_3Br$), N-iodosulfamic acid ($H_2NSO_3I$), N-chlorosulfamate ($HNSO_3Cl^-$), N-bromosulfamate ($HNSO_3Br^-$) N-iodosulfamate ($HNSO_3I^-$), N,N-dichlorosulfamic acid ($HNSO_3Cl_2$), N,N-dibromosulfamic acid ($HNSO_3Br_2$), N,N-diiodosulfamic acid ($HNSO_3I_2$), N-bromo-N-chlorosulfamic acid ($HNSO_3BrCl$), N-bromo-N-iodsulfamic acid ($HNSO_3BrI$), N-chloro-N-iodosulfamic acid ($HNSO_3ClI$), N,N-dichlorosulfamate ($NSO_3Cl_2^-$), N,N-dibromosulfamate ($NSO_3Br_2^-$), N,N-diiodosulfamate ($NSO_3I_2^-$), N-bromo-N-chlorosulfamate ($NSO_3BrCl^-$), N-bromo-N-iodosulfamate ($NSO_3BrI^-$), N-chloro-N-iodosulfamate ($NSO_3ClI^-$), or any combination of these components thereof.

The relative composition of free halogens, N-halosulfamic acids, N-halosulfamates, N,N-dihalosulfamic acids, and N,N-dihalosulfamates present in the electrolyzed solution will typically be determined by factors including, but not limited to, the relative composition of halide ions and sulfamic acid in the brine, and the pH of the electrolyzed solution. For example, the ratio of halide ion (and therefore eventual halogen content after electrolysis) to sulfamic acid in the brine will impact the relative distribution of free halogen, monohalogenated sulfamate species (N-halosulfamic acid and N-halosulfamate), and dihalogenated sulfamate species (N,N-dihalosulfamic acid and N,N-dihalosulfamate). In brines where there is an excess of sulfamic acid relative to the halide ion, the primary initial product will be monohalogenated sulfamate species; conversely, when the halide ion is in large excess of the sulfamic acid, the primary initial product of electrolysis will primarily be free halogen and dihalogenated sulfamate species. Similarly, the electrolyzed solution's pH can dictate the relative concentration of halosulfamic acids versus halosulfamate species, typically with higher halosulfamic acid composition at lower electrolyzed solution pH. Therefore, by varying the pH of brine prior to electrolysis, for example by varying the relative concentration of sulfamic acid and halides, the composition of the electrolyzed solution can be tailored as desired.

Organic sulfonamide, having a chemical formula of $RSO_2NH_2$ where R indicates the presence of an organic functional group such as, but not limited to, o-tolyl, m-tolyl, or p-tolyl, will behave in a similar fashion to sulfamic acid, in that N-halosulfonamide compounds having a chemical formula of $RSO_2NHX$, and N,N-dihalosulfonamide compounds having a chemical formula of $RSO_2NX_2$ and where X in both formulations represents a halogen, can be produced through this process. Similarly, mixtures of sulfamic acid and various organic sulfonamides can be used to produce mixtures of halosulfamate compounds and halosulfonamide compounds along with free halogen species of any desired composition. As with the above process, control over the composition of these complex solutions is preferably achieved by controlling the composition of the mixed brines used in the electrolysis process.

Alternatively, this process can utilize other halogen stabilizing chemical compounds besides or in addition to sulfamic acid and its derivatives. Typically, these chemicals comprise a molecule containing at least one nitrogen atom wherein the at least one nitrogen atom has a chemical bond to at least one hydrogen atom and the same nitrogen also has at least one chemical bond to an atom other than nitrogen, hydrogen, or a halogen. Examples of halogen stabilizing compounds that can be used for these purposes include, but are not limited to, cyanuric acid and its derivatives, succinimide and its derivatives, and hydantoin and its derivatives. Another example of a halogen stabilizing compound, phosphoramidic acid (a chemical having a formula of $H_4NPO_3$), can be used in place of or in addition to sulfamic acid in the practice of the present invention. Electrolysis of solutions containing at least phosphoramidic acid and at least one metal halide ion as described by the practice of the present invention can result in the production of free halogens, N-halophosphoramidic acid compounds (having a chemical formula of $H_3NPO_3X$), N-halophosphoramidate compounds (having a chemical formula of $H_2NPO_3X^-$ or $HNPO_3X^{2-}$), N,N-dihalophosphoramidic acid compounds (having a chemical formula of $H_2NPO_3X_2$), N,N-dihalophosphoramidate compounds (having a chemical formula of $HNPO_3X_2^-$ or $NPO_3X_2^{2-}$), or combinations thereof.

In the practice of the present invention, electrolysis is accomplished using an electrolytic cell comprising at least one cathode and at least one anode, although some embodiments of the present invention will also include several intermediate electrode plates to form a bipolar cell. Electrodes can be of any suitable material, but preferably Dimensionally Stable Anodes (which can be used as both the anode and cathode) are used in the present invention. Voltage applied to the electrolytic cell is preferably approximately 6V.

In the embodiment of the present invention shown in FIG. 1, tank 2 is a brine generator that is charged with a blended salt and water from a source (not shown). Here, the brine generator and a blended salt are used to produce a brine with continuous, near uniform composition which is transferred using pump 4 into line 6, which preferably also contains water. The diluted mixed brine is then transferred into generation system 8, which comprises an electrolytic cell along with a plurality of sensors and controls which monitor and alter the electrochemical process as needed to provide the desired product. The electrolyzed brine solution is then transferred through line 10 into tank 12, where the solution is stored until it is transferred to the application point.

Salt blends used in this embodiment of the present invention may include one or more metal halide compounds and at least sulfamic acid, but may also or alternatively include an organic sulfonamide or any other halogen stabilizing compound in any desired combination. Metal halide compounds useful here include, but are not limited to, sodium chloride, potassium chloride, sodium bromide, potassium bromide, sodium iodide, and potassium iodide. In addition to sulfamic acid, the organic sulfonamide component or halogen stabilizing component of the salt blend used in the present invention can include, but is not limited to, methylsulfonamide, o-toluenesulfonamide, m-toluenesulfonamide, p-toluenesulfonamide, cyanuric acid and its derivatives, succinimide and its derivatives, and hydantoin and its derivatives or any combination of these compounds. The ratio of metal halides to halogen stabilizing compounds in the blended salt used to prepare the brines is preferably carefully controlled in order to produce the desired aqueous solution comprising free halogen species, N-halosulfamate compounds, N,N-dihalosulfamate compounds, N-halosulfonamide compounds, N,N-dihalosulfonamide compounds, and any combination thereof in a highly stable, concentrated form.

Control over the brine content is preferably achieved by producing the salt blend as a pellet, briquette, or other compacted form, such that the individual components of the salt pellet or briquette are introduced into the brine at a predictable rate. Here, the salt blend preferably comprises at least one halide-containing salt combined with sulfamic acid and/or other halogen stabilizing agents as desired. The halide containing salt is preferably sodium chloride, although other halide containing salts can be used alone or in combination with sodium chloride. These salts include, but are not limited to, lithium chloride, potassium chloride, lithium bromide, sodium bromide, potassium bromide, lithium iodide, sodium iodide, and potassium iodide. Additional halogen stabilizing compounds that could be used in this embodiment of the present invention in addition to sulfamic acid include, but are not limited to, lithium sulfamate, sodium sulfamate, potassium sulfamate, o-toluenesulfonamide, m-toluenesulfonamide, p-toluenesulfonamide, cyanuric acid and its derivatives, succinimide and its derivatives, and hydantoin and its derivatives. In one embodiment a metal halide salt is preferably combined with sulfamic acid to form a solid solution. The sulfamic acid is preferably no more than approximately 30% by weight of the solid solution and the metal halide is preferably at least approximately 70% by weight of the solid solution. The components are preferably thoroughly mixed and evenly dispersed throughout the solid solution. Additionally, other components, such as anticaking components, can be added to this mixture. When diluted, this salt blend produces a brine with a predictable and steady composition which can be used to produce, through electrolysis and the subsequent chemical transformations described above, the desired product biocidal solutions.

Alternatively, brines with a desired composition can be formulated and used as an aqueous solution. In such embodiments the brine preferably comprises a halide containing salt and sulfamic acid dissolved in water at the desired concentrations and in the desired ratio of halide ion to sulfamic acid. The halide containing salt is preferably sodium chloride, although any other halide containing salt could be used in this embodiment of the present invention either alone or in combination with sodium chloride. These salts include, but are not limited to, lithium chloride, potassium chloride, lithium bromide, sodium bromide, potassium bromide, lithium iodide, sodium iodide, and potassium iodide. Additionally, other halogen stabilizing compounds can be added to these brines in addition to the sulfamic acid. These halogen stabilizing compounds can include, but are not limited to, lithium sulfamate, sodium sulfamate, potassium sulfamate, o-toluenesulfonamide, m-toluenesulfonamide, p-toluenesulfonamide, cyanuric acid and its derivatives, succinimide and its derivatives, and hydantoin and its derivatives.

The present invention preferably does not require the addition of a non-amine base to produce the desired halosulfamate or halosulfamic acid solution. In U.S. Pat. No. 3,776,825, Vit discloses that electrolytically produced aqueous solutions of chloramines having a pH in the range of 8 to 12 require the use of a brine made from a combination of a salt containing at least one halide ion, at least one amine compound and, importantly, a hydroxide compound used in molar excess of the amine compound which is required for pH control. In the examples disclosed by Vit, the pH of the brines used to prepare the desired aqueous organic haloamine solutions were all greater than 12 (calculated from the numbers presented by Vit). In contrast, the present invention preferably is performed with an initial brine pH of less than 12, and more preferably less than 10, and even more preferably less than 7, and even more preferably less than 4, and even more preferably less than 2, and even more preferably less than 1.

Figure 2:
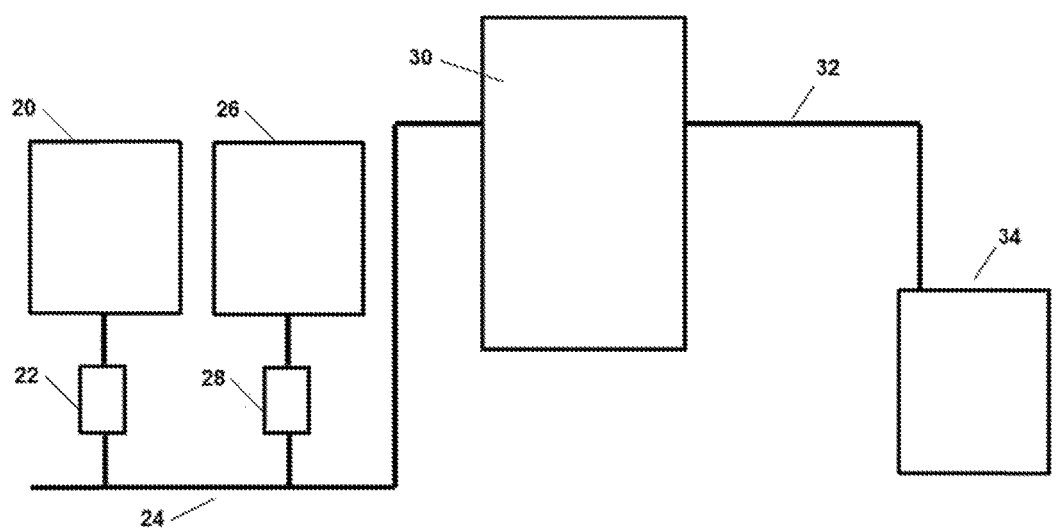
FIG. 2 is a schematic drawing of a system for the production of stable, concentrated aqueous solutions comprised of free halogen species, N-halosulfamate compounds, N,N-dihalosulfamate compounds, N-halosulfonamide compounds, N,N-dihalosulfonamide compounds from a dual, highly concentrated brine sources that are diluted into a process water.

An alternative embodiment of the present invention is shown in FIG. 2. In this embodiment of the present invention, tank 20 is a brine generator where the brine formed by the generator comprises metal halide salts substantially without sulfamic and is fed with water from a source (not shown). Similarly, tank 26 is also a brine generator where the brine formed by the generator sulfamic acid substantially without metal halide salts, organic sulfonamide compounds, or combinations thereof. Brine produced in tank 20 is transferred to line 24 through the action of pump 22 while the brine produced in tank 26 is also transferred to line 24 through the action of pump 28. Line 24 also preferably contains water from a source not shown here, which serves to dilute the brines from tank 20 and tank 24 to the desired concentration. The diluted brine stream then enters generation system 30 wherein the desired biocidal solution is produced and is then transferred through line 32 to tank 34. The electrolyzed solution is then stored in tank 34 until it is transferred to the application point.

The embodiment depicted in FIG. 2 could optionally utilize a multitude of brine generator tanks and injection pumps to provide a further degree of control over the composition of the brine solution used in this process. For example, separate brine generation tanks could contain singular metal halide salts, sulfamic acid, and organic sulfonamide compounds which could be selectively and individually injected into the brine stream entering generator system 30 in any desired composition, thereby producing a biocidal solution of any desired composition. This embodiment of the present invention would be advantageous in applications were several biocidal solutions or different compositions are required for different water treatment applications within a single facility, with the desired solution begin able to be produced on demand by simply varying the amounts of the different components of the brine solution. A plurality of product tanks could optionally be utilized so that each specifically desired biocidal solution could be stored and applied separately.

Figure 3:
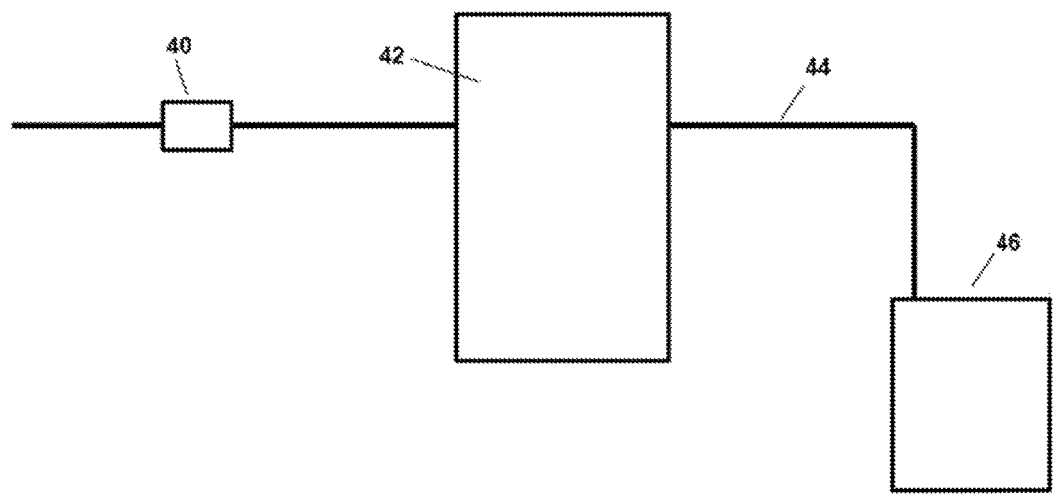
FIG. 3 is a schematic drawing of a system for the production of stable, concentrated aqueous solutions comprised of free halogen species, N-halosulfamate compounds, N,N-dihalosulfamate compounds, N-halosulfonamide compounds, N,N-dihalosulfonamide compounds from a single source brine.

An alternative embodiment of the present invention is shown in FIG. 3. In this embodiment, brine from a source not shown here is transferred through the action of pump 40 into generation system 42. In this embodiment, the brine is at a ready-to-use concentration and does not need to be diluted by process water as shown in the other embodiments of the present invention. Once the brine is in generation system 42, the brine is electrolyzed and transferred out of generation system 42 along line 44 and into tank 46, where the electrolyzed solution is stored until needed and transferred out of tank 46 using a mechanism not shown here.

The generation systems described above preferably comprise the electrochemical cell(s) in which the electrochemical oxidation of halide ions to aqueous halogens occurs. Once the aqueous halogen species is formed, it is free to react with sulfamic acid, producing the desired biocidal solution containing a combination of free halogen species, N-halosulfamate, N-halosulfamic acid, N,N-dihalosulfamate, and N,N-dihalosulfamic acid. A plurality of sensors and control systems (not shown) are preferably used by the present invention to ensure that the proper brine composition is utilized by generator system 8 or generator system 30 to produce the desired biocidal solution.

In the practice of all embodiments of the present invention, it is possible to control the composition of the electrolyzed solution by varying the composition of the brine used in the production process as well as the overall flow through the electrolytic cell. For example, by varying the molar ratio of the total halide ion content of the brine to the sulfamic acid or total sulfamic acid and other stabilizer component of the brine, it is possible to produce solutions which comprise the desired amount of free halogen and stabilized halogen species. Moreover, it is also possible to achieve control over the pH of the electrolyzed solution by varying this ratio as well, so that low pH oxidant solutions can be produced when the ratio of sulfamic acid to total halide ion content is high enough. Similarly, in cases where a biocidal solution comprising two or more halogen species is desirable, it is possible to control the ratio of halogen in the biocidal solution by varying the ratio of different halide ions in the brine.

Electrolysis operational parameters can also be used to vary the composition of the electrolyzed solution, primarily through adjusting the flow rate through the electrolytic cell. Under low flow conditions, electrolyzed solutions at high pH and increased combined halogen content are typically produced, while at higher flow rates, the electrolyzed solution is typically produced at low pH and decreased combined halogen content, even though the brine concentration is the same. This unexpected finding can be very useful in the practice of the present invention, for example by providing a method by which the electrolytic cell can be self-cleaned. It is well known in the art that the electrolysis of halide containing brines will result in the formation of scales on the cathode surfaces. These scales typically comprise calcium carbonate, although magnesium hydroxide, iron oxide, and manganese oxide scales can also form on the cathode. Scale formation on the cathodes is primarily driven by the low pH environment at the cathode surface, and it is well known in the art that acid can be used to remove scales from the cathode surfaces. In the practice of the present invention, it is possible to automatically remove the scale from the electrode surface while continuing the production of the desired biocidal solution by simply increasing the flow of the brine through the cell such that an acidic oxidant solution is produced, thereby cleaning the scale from the electrode surfaces. The composition of the electrolyzed product produced during the cleaning cycle would be different than the composition of the electrolyzed product produced during normal operation of the system.

In general, embodiments of the present invention can produce a solution that has a total halogen content of less than 500 mg/L, more preferably less than 1000 mg/L, even more preferably less than 2100 mg/L, even more preferably more than 2100 mg/L, even more preferably more than 2500 mg/L, and even more preferably more than 3000 mg/L. In addition, embodiments of the present invention can be tailored so that the pH of the electrolyzed solution can be quite high even though the pH of the brine prior to electrolysis is very low.

The following examples demonstrate that varying the brine composition as well as the electrolysis operational parameters define the composition of the electrolyzed solution.

EXAMPLE 1

Using an electrochemical system similar to the one depicted in FIG. 3, brines containing a mixture of sodium chloride and sulfamic acid were electrolyzed at an applied plate-to-plate voltage of 6 V to produce solutions comprising free chlorine species, N-chlorosulfamate, N-chlorosulfamic acid, N,N-dichlorosulfamate, and N,N-dichlorosulfamic acid. Brines used in this example were prepared with a sodium chloride content of 30 g/L in every brine along with a sulfamic acid content of between 1 and 12 g/L. All brines prepared for this test had a pH of 2.12 or less. After electrolysis, the free chlorine content (representing only chlorine, hypochlorous acid, and hypochlorite ions) was measured alongside the total chlorine content, which measured free chlorine species as well as N-chlorosulfamate, N-chlorosulfamic acid, N,N-dichlorosulfamate, and N,N-dichlorosulfamic acid. These results are given in Table 1 below. As can be seen, the relative composition of the electrolyzed solution varies as a function of the sulfamic acid content in the initial brine. Moreover, when the sulfamic acid content of the brine was ~12% and higher, the electrolyzed solution primarily comprised N-chlorosulfamate, N-chlorosulfamic acid, N,N-dichlorosulfamate, and N,N-dichlorosulfamic acid, with very few free chlorine species present.

along with a sulfamic acid content of between 0 and 10 g/L, resulting in brines comprising between 0% and 12% by weight sulfamic acid, 18% to 20% by weight sodium bromide, and 71% to 80% by weight sodium chloride. Brines containing sulfamic acid in this example had a pH of 2.04 or less. After electrolysis, the free halogen content, represent-

TABLE 1

| Sulfamic acid content in the brine (%) | Brine pH | Free chlorine content in the electrolyzed solution (mg/L) | Total chlorine content in the electrolyzed solution (mg/L) | Electrolyzed solution pH | Percent free chlorine in the electrolyzed solution (%) | Percent N-chlorosulfamate, N-chlorosulfamic acid, N,N-dichlorosulfamate, and N,N-dichlorosulfamic acid in the electrolyzed solution (%) |
|---|---|---|---|---|---|---|
| 3  | 2.12 | 2675 | 3950 | 11.28 | 68 | 32 |
| 6  | 1.81 | 1650 | 4025 | 11.48 | 41 | 59 |
| 9  | 1.63 | 400  | 3925 | 11.40 | 10 | 90 |
| 12 | 1.53 | 175  | 3850 | 10.48 | 5  | 95 |
| 14 | 1.45 | 190  | 4000 | 9.96  | 5  | 95 |
| 17 | 1.39 | 85   | 4300 | 9.40  | 2  | 98 |
| 19 | 1.33 | 135  | 4475 | 2.39  | 3  | 97 |
| 21 | 1.26 | 115  | 4825 | 1.90  | 2  | 98 |
| 23 | 1.25 | 130  | 4950 | 1.63  | 3  | 97 |
| 29 | 1.19 | 70   | 5200 | 1.48  | 1  | 99 |

EXAMPLE 2

Electrolysis of brines containing mixed halide ions and sulfamic acid can be utilized to produce complex disinfection solutions containing mixed halogen, halosulfamic acid, and halosulfamate compounds. Using an electrochemical system similar to the one depicted in FIG. 3, brines containing a mixture of sodium chloride and sulfamic acid were electrolyzed at an applied plate-to-plate voltage of 6 V to produce solutions comprised of free chlorine species, N-halosulfamate, N-halosulfamic acid, N,N-dihalosulfamate, and N,N-dihalosulfamic acid. In this example, N-halosulfamate can be either N-chlorosulfamate or N-bromosulfamate, N-halosulfamic acid can be either N-chlorosulfamic acid or N-bromosulfamic acid, N,N-dihalosulfamate can be N,N-dichlorosulfamate, N,N-dibromosulfamate, or N-bromo-N-chlorosulfamate, and N,N-dihalosulfamic acid can be N,N-dichlorosulfamic acid, N,N-dibromosulfamic acid, or N-bromo-N-chlorosulfamic acid. Brines used in this example were prepared with a sodium chloride content of 24 g/L and a sodium bromide content of 6 g/L in every brine ing the content of chlorine, hypochlorous acid, hypochlorite ions, bromine, hypobromous acid, and hypobromite ions was measured. The free bromine content, measuring only the presence of bromine, hypobromous acid, and hypobromite ions was also measured along with the total halogen content, which measured all free halogen species along with the N-halosulfamate, N-halosulfamic acid, N,N-dihalosulfamate, and N,N-dihalosulfamic acid content. These results are given in Table 2 below. As can be seen in this data, increasing the amount of sulfamic acid in the brine decreased the free halogen percentage in the electrolyzed brine while the percentage of the N-halosulfamate, N-halosulfamic acid, N,N-dihalosulfamate, and N,N-dihalosulfamic acid content increased correspondingly. Unexpectedly, the bulk of the free halogen content in all brines with added sulfamic acid was found to be free bromine species.

TABLE 2

| Sodium Chloride content in the brine (%) | Sodium Bromide content in the brine (%) | Sulfamic acid content in the brine (%) | Brine pH | Free halogen content in the electrolyzed solution (mg/L (%)) | Free bromine content of the free halogen in the electrolyzed solution (mg/L (%)) | Total halogen content in the electrolyzed solution (mg/L (%)) | Electrolyzed Solution pH |
|---|---|---|---|---|---|---|---|
| 80 | 20 | 0  | 6.94 | 3600 (100) | 2750 (76) | Not Applicable | 9.87  |
| 77 | 19 | 3  | 2.04 | 3200 (85)  | 2400 (75) | 3750 (15) | 11.18 |
| 75 | 19 | 6  | 1.77 | 2600 (70)  | 2400 (92) | 3700 (30) | 11.23 |
| 73 | 18 | 9  | 1.58 | 1925 (53)  | 1825 (95) | 3625 (47) | 11.06 |
| 71 | 18 | 12 | 1.48 | 2125 (53)  | 1850 (87) | 4025 (47) | 10.53 |

EXAMPLE 3

Stability of solutions produced through the electrolysis of brines containing mixed halide ions and sulfamic acid was examined using the same procedure outlined in Example 2.

Here, using an electrochemical system similar to the one depicted in FIG. 3, brines containing a mixture of sodium chloride, sodium bromide, and sulfamic acid were electrolyzed at an applied plate-to-plate voltage of 6 V to produce solutions comprised of free chlorine species, N-halosulfamate, N-halosulfamic acid, N,N-dihalosulfamate, and N,N-dihalosulfamic acid. Brines used in this example were prepared with a sodium chloride content of 24 g/L and a sodium bromide content of 6 g/L in every brine along with a sulfamic acid content of between 0 and 6 g/L, giving brines comprised of between 0% and 9% by weight sulfamic acid, 18% to 20% by weight sodium bromide, and 73% to 80% by weight sodium chloride. Brines used in this example had a pH of 2.09 or less. Total halogen content of these solutions was measured immediately after electrolysis as well as after the electrolyzed solutions were stored for 24 hours. These results are shown in Table 3, where it can be seen that the addition of even 3% sulfamic acid to the electrolyzed brine confers a high degree of stability on the total halogen content of the electrolyzed solution compared to solutions where sulfamic acid was not added. Additionally, the compositions of the chlorine and bromine components of the free halogen species of these solutions were also measured both immediately after electrolysis and after storage for 24 hours. These results, given in Table 4, show that for all solutions tested, the relative amount of bromine in the free halogen content of the electrolyzed brines increases during aging, indicating that a continuous oxidation process of bromide ions during storage is occurring.

in this example typically had a pH of less than 1. After electrolysis, the pH of the electrolyzed solution was measured alongside the total chlorine content, which measured free chlorine species as well as N-chlorosulfamate, N-chlorosulfamic acid, N,N-dichlorosulfamate, and N,N-dichlorosulfamic acid. These results are given in Table 5 below. When the brine sulfamic acid content was 150 g/L or lower, the pH of the electrolyzed solution was 9.28 or higher. However, when the sulfamic acid content was increased to above 150 g/L, the pH of the electrolyzed solution rapidly decreased to as low as 2.03. Thus the final composition of the electrolyzed solution can be varied depending on even small changes in the sulfamic acid content of the brine.

TABLE 5

| Sulfamic acid content in the brine (g/L) | Total halogen content in the electrolyzed solution (mg/L) | pH of the electrolyzed solution |
|---|---|---|
| 0 | 3100 | 9.28 |
| 10 | 3300 | 10.79 |
| 20 | 3350 | 11.14 |
| 30 | 3325 | 11.41 |
| 40 | 3475 | 11.46 |
| 50 | 3650 | 11.55 |
| 60 | 3550 | 11.59 |
| 70 | 3525 | 11.62 |
| 80 | 3525 | 11.69 |
| 90 | 3525 | 11.64 |

TABLE 3

| Sulfamic acid content in the brine (%) | Brine pH | Total halogen content in the electrolyzed solution immediately after electrolysis (mg/L) | Total halogen content in the electrolyzed solution after 24 hours of storage (mg/L) | Percent loss of the total halogen content after storage for 24 hours (%) | Electrolyzed solution pH |
|---|---|---|---|---|---|
| 0 | 6.82 | 3375 | 450 | 87 | 9.91 |
| 3 | 2.09 | 3400 | 3400 | 0 | 11.12 |
| 9 | 1.62 | 3350 | 3200 | 4 | 11.13 |

TABLE 4

| Sulfamic acid content in the brine (%) | Free halogen content in the electrolyzed brine | | Free bromine content in the electrolyzed brine | | Free bromine content of the free halogen in the electrolyzed brine (%) | |
|---|---|---|---|---|---|---|
| | Immediately after electrolysis | After storage for 24 hours | Immediately after electrolysis | After storage for 24 hours | Immediately after electrolysis | After storage for 24 hours |
| 0 | 3100 | 450 | 2125 | 375 | 69 | 83 |
| 3 | 2850 | 2975 | 1925 | 2350 | 68 | 79 |
| 9 | 2050 | 2275 | 1825 | 2175 | 89 | 96 |

EXAMPLE 4

Using an electrochemical system similar to the one depicted in FIG. 1, brines containing a mixture of sodium chloride and sulfamic acid were combined with process flow water and electrolyzed at an applied plate-to-plate voltage of 6 V to produce solutions comprising free chlorine species, N-chlorosulfamate, N-chlorosulfamic acid, N,N-dichlorosulfamate, and N,N-dichlorosulfamic acid. Brines used in this example were prepared with >99% saturated aqueous sodium chloride with sulfamic acid added at a concentration of between 0 and 200 g/L. Brines containing sulfamic acid TABLE 5-continued

| Sulfamic acid content in the brine (g/L) | Total halogen content in the electrolyzed solution (mg/L) | pH of the electrolyzed solution |
|---|---|---|
| 100 | 3475 | 11.44 |
| 110 | 3375 | 11.18 |
| 120 | 3350 | 10.99 |
| 130 | 3075 | 10.43 |
| 140 | 3050 | 10.16 |

TABLE 5-continued

| Sulfamic acid content in the brine (g/L) | Total halogen content in the electrolyzed solution (mg/L) | pH of the electrolyzed solution |
|---|---|---|
| 150 | 3125 | 9.76 |
| 160 | 3050 | 5.34 |
| 170 | 2775 | 2.33 |
| 180 | 2975 | 2.68 |
| 190 | 2725 | 2.16 |
| 200 | 2575 | 2.03 |

EXAMPLE 5

Using an electrochemical system similar to the one depicted in FIG. 1, brines containing a mixture of sodium chloride and sulfamic acid were combined with process flow water and electrolyzed at an applied plate-to-plate voltage of 6 V to produce solutions comprising free chlorine species, N-chlorosulfamate, N-chlorosulfamic acid, N,N-dichlorosulfamate, and N,N-dichlorosulfamic acid. Brines used in this example were prepared with >99% saturated aqueous sodium chloride with sulfamic acid added to a concentration of 80 g/L, with the brine having a pH of less than 1. In this example, the total flow of water through the system was varied between 19.6 and 44.9 gallons per hour. After electrolysis, the pH of the electrolyzed solution was measured alongside the total chlorine content, which measured free chlorine species as well as N-chlorosulfamate, N-chlorosulfamic acid, N,N-dichlorosulfamate, and N,N-dichlorosulfamic acid. These results are given in Table 6 below. Unexpectedly, the pH of the electrolyzed solution was highly dependent on total flow rate. Under low flow conditions (24.4 gal/hr or lower), the pH of the electrolyzed solution was higher than 10.25. In the transition flow range of 28.5 to 32.0 gal/hr, the pH of the electrolyzed solution was more moderate with a range of 3.90 to 8.86. When the flow was 33.3 gal/hr or higher, the pH of the electrolyzed solution was highly acidic and lower than 2.81, and as low as 2.05.

TABLE 6

| Water Flow Rate (gal/hr) | pH the electrolyzed solution | Total halogen content in the electrolyzed solution (mg/L) |
|---|---|---|
| 19.6 | 11.46 | 4108 |
| 21.5 | 10.79 | 3808 |
| 24.4 | 10.25 | 3400 |
| 28.5 | 8.86 | 2767 |
| 30.9 | 7.54 | 2867 |
| 32.0 | 3.90 | 2667 |
| 33.3 | 2.81 | 2633 |
| 34.3 | 2.73 | 2525 |
| 36.7 | 2.13 | 2392 |
| 39.1 | 2.09 | 2308 |
| 42.0 | 2.05 | 2242 |
| 44.9 | 2.06 | 2042 |

Although the invention has been described in detail with particular reference to the disclosed embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. A method for producing a stable disinfecting solution comprising a plurality of halosulfamate species and/or halosulfamic acid species and one or more halogen species, the method comprising:
   preparing an aqueous acidic solution comprising halide ions and sulfamic acid and having a pH of less than 7; and
   electrolyzing said aqueous acidic solution to produce the stable disinfecting solution, wherein the concentrations of the halide ions and the sulfamic acid in said aqueous acidic solution and the pH of said aqueous acidic solution being such as to produce the stable disinfecting solution having a total halogen content of at least 2100 mg/L and exhibiting less than 5% loss of halogen content over a 24 hour time period.

2. The method of claim 1, wherein the aqueous acidic solution further comprises one or more additional halogen stabilizing compounds.

3. The method of claim 2, wherein the one or more additional halogen stabilizing compounds are selected from the group consisting of lithium sulfamate, sodium sulfamate, potassium sulfamate, organic sulfonamide, methylsulfonamide, o-toluenesulfonamide, m-toluenesulfonamide, p-toluenesulfonamide, cyanuric acid, a derivative of cyanuric acid, succinimide, a derivative of succinimide, hydantoin, a derivative of hydantoin, and combinations thereof.

4. The method of claim 3, wherein the stable disinfecting solution comprises N-halosulfonamide compounds and/or N,N-dihalosulfonamide compounds.

5. The method of claim 1, wherein the halosulfamate species comprise N-halosulfamate compounds and/or N,N-dihalosulfamate compounds.

6. The method of claim 1, wherein the halosulfamic acid species comprise N-halosulfamic acid compounds and/or N,N-dihalosulfamic acid compounds.

7. The method of claim 1, wherein the stable disinfecting solution has a total halogen content of at least 2500 mg/L.

8. The method of claim 1, wherein the aqueous acidic solution does not comprise a non-amine base.

9. The method of claim 1, wherein the preparing step comprises:
   providing a salt blend comprising sulfamic acid and one or more salts comprising the halide ions; and
   diluting the salt blend with water.

10. The method of claim 9, wherein the salt blend comprises a pellet, briquette, or compacted form.

11. The method of claim 9, wherein the salt blend comprises a solid solution.

12. The method of claim 9, wherein the salt blend comprises an anti-caking agent.

13. The method of claim 1, further comprising flowing the aqueous acidic solution through an electrolytic cell at a flow rate selected to produce the desired pH of the stable disinfecting solution.

14. The method of claim 13, further comprising increasing the flow rate, thereby maintaining the acidity of electrolyte in the vicinity of cathodes in the electrolytic cell during the electrolyzing step.

15. The method of claim 14, further comprising removing scale from surfaces of the cathodes or preventing the formation of scale on the surfaces of the cathodes.

16. The method of claim 1, wherein the pH of the aqueous acidic solution is less than 4.

17. The method of claim 16, wherein the pH of the aqueous acidic solution is less than 2.

18. The method of claim 1, wherein the pH of the stable disinfecting solution is greater than 9.

19. The method of claim 18, wherein the pH of the stable disinfecting solution is greater than 11.

20. The method of claim 1, wherein the pH of the stable disinfecting solution is less than 3.

* * * * *